United States Patent
Harandi et al.

(10) Patent No.: US 10,407,631 B2
(45) Date of Patent: *Sep. 10, 2019

(54) GASIFICATION WITH ENRICHED OXYGEN FOR PRODUCTION OF SYNTHESIS GAS

(71) Applicant: ExxonMobil Research and Engineering Company, Annandale, NJ (US)

(72) Inventors: Mohsen N. Harandi, New Hope, PA (US); Suriyanarayanan Rajagopalan, Spring, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/812,340

(22) Filed: Nov. 14, 2017

(65) Prior Publication Data

US 2019/0144768 A1   May 16, 2019

(51) Int. Cl.
*B01J 8/26* (2006.01)
*C01C 1/04* (2006.01)
(Continued)

(52) U.S. Cl.
CPC ............. *C10J 3/466* (2013.01); *B01J 8/26* (2013.01); *C01C 1/0405* (2013.01);
(Continued)

(58) Field of Classification Search
CPC ............ C10J 3/466; C10J 2300/0943; C10J 2300/0959; C10J 2300/0976;
(Continued)

(56) References Cited

U.S. PATENT DOCUMENTS 3,261,775 A    7/1966  Blaser
3,354,078 A    11/1967 Miale et al.
(Continued)

FOREIGN PATENT DOCUMENTS

WO    2013/062800 A1    5/2013

OTHER PUBLICATIONS

Database of Zeolite Structures, Structure Commission of the International Zeolite Association, Jun. 27, 2018, www.iza-structure.org/databases.
(Continued)

*Primary Examiner* — Jafar F Parsa
(74) *Attorney, Agent, or Firm* — Hsin Lin

(57) ABSTRACT

Systems and methods are provided for producing high quality synthesis gas from a fluidized coking system that includes an integrated gasifier. Additionally or alternately, systems and methods are provided for integrating a fluidized coking process, a coke gasification process, and processes for production of compounds from the synthesis gas generated during the coke gasification. The integrated process can also allow for reduced or minimized production of inorganic nitrogen compounds by using oxygen from an air separation unit as the oxygen source for gasification. Although the amount of nitrogen introduced as a diluent into the gasification will be reduced, minimized, or eliminated, the integrated process can also allow for gasification of coke while reducing, minimizing, or eliminating production of slag or other glass-like substances in the gasifier. Examples of compounds that can be produced from the synthesis gas include, but are not limited to, methanol, ammonia, and urea.

14 Claims, 3 Drawing Sheets

(51) Int. Cl.
*C10J 3/46* (2006.01)
*C10J 3/48* (2006.01)
*C10J 3/82* (2006.01)
*C07C 273/10* (2006.01)
*C07C 29/151* (2006.01)

(52) U.S. Cl.
CPC ........ *C07C 29/1518* (2013.01); *C07C 273/10* (2013.01); *C10J 3/485* (2013.01); *C10J 3/82* (2013.01); *B01J 2208/00752* (2013.01); *C10J 2300/0903* (2013.01); *C10J 2300/0943* (2013.01); *C10J 2300/0959* (2013.01); *C10J 2300/1665* (2013.01); *C10J 2300/1668* (2013.01)

(58) Field of Classification Search
CPC .... C10J 2300/1838; C10G 9/005; C10G 1/02; C10G 9/32; C07C 273/10; C07C 273/04; C01C 1/0488
See application file for complete search history.

(56) References Cited

U.S. PATENT DOCUMENTS

| | | |
|---|---|---|
| 3,661,543 A | 5/1972 | Saxton |
| 3,702,516 A | 11/1972 | Luckenbach |
| 3,702,886 A | 11/1972 | Argauer et al. |
| 3,709,979 A | 1/1973 | Chu |
| 3,726,791 A | 4/1973 | Kimberlin et al. |
| 3,752,658 A | 8/1973 | Blaser |
| 3,759,676 A | 9/1973 | Lahn |
| 3,816,084 A | 6/1974 | Moser et al. |
| 4,016,218 A | 4/1977 | Haag et al. |
| RE29,948 E | 3/1979 | Dwyer et al. |
| 4,213,848 A | 7/1980 | Saxton |
| 4,269,696 A | 5/1981 | Metrailer |
| 4,295,956 A | 10/1981 | Metrailer |
| 4,433,185 A | 2/1984 | Tabak |
| 4,456,779 A | 6/1984 | Owen et al. |
| 4,497,968 A | 2/1985 | Wright et al. |
| 4,547,616 A | 10/1985 | Avidan et al. |
| 4,579,999 A | 4/1986 | Gould et al. |
| 4,582,815 A | 4/1986 | Bowes |
| 4,587,010 A | 5/1986 | Blaser et al. |
| 4,751,338 A | 6/1988 | Tabak et al. |
| 4,827,069 A | 5/1989 | Kushnerick et al. |
| 4,899,002 A | 2/1990 | Harandi et al. |
| 4,992,607 A | 2/1991 | Harandi et al. |
| 5,176,819 A | 1/1993 | Green |
| 5,472,596 A | 12/1995 | Kerby |
| 6,448,441 B1 | 9/2002 | Wing-Chiu et al. |
| 7,919,065 B2 | 4/2011 | Pedersen |
| 9,090,525 B2 | 7/2015 | Brown |
| 9,234,146 B2 | 1/2016 | Koseoglu |
| 2012/0006723 A1 | 1/2012 | Davis et al. |
| 2012/0055088 A1 | 3/2012 | Steele et al. |
| 2015/0183650 A1* | 7/2015 | Younes ................ C01C 1/0417 564/69 |
| 2017/0233667 A1 | 8/2017 | Harandi et al. |

OTHER PUBLICATIONS

Kamienski et al., "Coking Without the Coke", Hydrocarbon Engineering, Mar. 2008.
Miale et al., "Catalysis by Crystalline Aluminosilicates", Journal of Catalysis, 1966, vol. 6, pp. 278-287.
Olson et al., "Chemical and Physical Properties of the ZSM-5 Substituional Series", Journal of Catalysis, vol. 61, 1980, pp. 390-396.
Weisz et al., "Superactive Crystalline Aluminosilicate Hydrocarbon Catalysts", Journal of Catalysis, 1965, vol. 4, pp. 527-529.
Zhao et al., "Coal to Clean Gasoline", Hydrocarbon Engineering, Mar. 2008.
The International Search Report and Written Opinion of PCT/US2018/059523 dated Apr. 24, 2019.
The International Search Report and Written Opinion of PCT/US2018/059527 dated Apr. 24, 2019.

* cited by examiner

GASIFICATION WITH ENRICHED OXYGEN FOR PRODUCTION OF SYNTHESIS GAS

CROSS-REFERENCE TO RELATED APPLICATIONS

This application is related to one other co-pending U.S. application, filed on even date herewith, and identified by the following Ser. No. 15/812,396 entitled "Fluidized Coking with Increased Production of Liquids". This co-pending U.S. application is hereby incorporated by reference in its entirety.

FIELD

Systems and methods are provided for production of synthesis gas in a fluidized coking process and integration with production of compounds from synthesis gas.

BACKGROUND

Coking is a carbon rejection process that is commonly used for upgrading of heavy oil feeds and/or feeds that are challenging to process, such as feeds with a low ratio of hydrogen to carbon. In addition to producing a variety of liquid products, typical coking processes can also generate a substantial amount of coke. Because the coke contains carbon, the coke is potentially a source of additional valuable products in a refinery setting. However, fully realizing this potential remains an ongoing challenge.

Coking processes in modern refinery settings can typically be categorized as delayed coking or fluidized bed coking. Fluidized bed coking is a petroleum refining process in which heavy petroleum feeds, typically the non-distillable residues (resids) from the fractionation of heavy oils are converted to lighter, more useful products by thermal decomposition (coking) at elevated reaction temperatures, typically about 480° C. to 590° C., (about 900° F. to 1100° F.) and in most cases from 500° C. to 550° C. (about 930° F. to 1020° F.). Heavy oils which may be processed by the fluid coking process include heavy atmospheric resids, petroleum vacuum distillation bottoms, aromatic extracts, asphalts, and bitumens from tar sands, tar pits and pitch lakes of Canada (Athabasca, Alta.), Trinidad, Southern Calif. (La Brea (Los Angeles), McKittrick (Bakersfield, Calif.), Carpinteria (Santa Barbara County, Calif.), Lake Bermudez (Venezuela) and similar deposits such as those found in Texas, Peru, Iran, Russia and Poland.

Fluidized coking is carried out in a unit with a large reactor containing hot coke particles which are maintained in the fluidized condition at the required reaction temperature with steam injected at the bottom of the vessel with the average direction of movement of the coke particles being downwards through the bed. The heavy oil feed is heated to a pumpable temperature, typically in the range of 350° C. to 400° C. (about 660° F. to 750° F.), mixed with atomizing steam, and fed through multiple feed nozzles arranged at several successive levels in the reactor. Steam is injected into a stripping section at the bottom of the reactor and passes upwards through the coke particles descending through the dense phase of the fluid bed in the main part of the reactor above the stripping section. Part of the feed liquid coats the coke particles in the fluidized bed and is subsequently cracked into layers of solid coke and lighter products which evolve as gas or vaporized liquid. Reactor pressure is relatively low in order to favor vaporization of the hydrocarbon vapors which pass upwards from dense phase into dilute phase of the fluid bed in the coking zone and into cyclones at the top of the coking zone where most of the entrained solids are separated from the gas phase by centrifugal force in one or more cyclones and returned to the dense fluidized bed by gravity through the cyclone diplegs. The mixture of steam and hydrocarbon vapors from the reactor is subsequently discharged from the cyclone gas outlets into a scrubber section in a plenum located above the coking zone and separated from it by a partition. It is quenched in the scrubber section by contact with liquid descending over sheds, A pumparound loop circulates condensed liquid to an external cooler and back to the top shed row of the scrubber section to provide cooling for the quench and condensation of the heaviest fraction of the liquid product. This heavy fraction is typically recycled to extinction by feeding back to the coking zone in the reactor.

The coke particles formed in the coking zone pass downwards in the reactor and leave the bottom of the reactor vessel through a stripper section where they are exposed to steam in order to remove occluded hydrocarbons. The solid coke from the reactor, consisting mainly of carbon with lesser amounts of hydrogen, sulfur, nitrogen, and traces of vanadium, nickel, iron, and other elements derived from the feed, passes through the stripper and out of the reactor vessel to a burner or heater where it is partly burned in a fluidized bed with air to raise its temperature from about 480° C. to 700° C. (about 900° F. to 1300° F.) to supply the heat required for the endothermic coking reactions, after which a portion of the hot coke particles is recirculated to the fluidized bed reaction zone to transfer the heat to the reactor and to act as nuclei for the coke formation. The balance is withdrawn as coke product. The net coke yield is only about 65 percent of that produced by delayed coking.

The Flexicoking™ process, developed by Exxon Research and Engineering Company, is a variant of the fluid coking process that is operated in a unit including a reactor and a heater, but also including a gasifier for gasifying the coke product by reaction with an air/steam mixture to form a low heating value fuel gas. A stream of coke passes from the heater to the gasifier where all but a small fraction of the coke is gasified to a low-BTU gas (~120 BTU/standard cubic feet) by the addition of steam and air in a fluidized bed in an oxygen-deficient environment to form fuel gas comprising carbon monoxide and hydrogen. In a conventional Flexicoking™ configuration, the fuel gas product from the gasifier, containing entrained coke particles, is returned to the heater to provide most of the heat required for thermal cracking in the reactor with the balance of the reactor heat requirement supplied by combustion in the heater. A small amount of net coke (about 1 percent of feed) is withdrawn from the heater to purge the system of metals and ash. The liquid yield and properties are comparable to those from fluid coking. The fuel gas product is withdrawn from the heater following separation in internal cyclones which return coke particles through their diplegs.

The Flexicoking process is described in patents of Exxon Research and Engineering Company, including, for example, U.S. Pat. No. 3,661,543 (Saxton), U.S. Pat. No. 3,759,676 (Lahn), U.S. Pat. No. 3,816,084 (Moser), U.S. Pat. No. 3,702,516 (Luckenbach), U.S. Pat. No. 4,269,696 (Metrailer). A variant is described in U.S. Pat. No. 4,213,848 (Saxton) in which the heat requirement of the reactor coking zone is satisfied by introducing a stream of light hydrocarbons from the product fractionator into the reactor instead of the stream of hot coke particles from the heater. Another variant is described in U.S. Pat. No. 5,472,596 (Kerby) using a stream of light paraffins injected into the hot coke return line to generate olefins. Early work proposed units with a stacked configuration but later units have migrated to a side-by-side arrangement.

Although the fuel gas from the gasifier can be used for heating, due to the low energy content, burning of the fuel gas for heat can still represent a relatively low value use for the carbon in the fuel gas. What is needed are systems and methods that can allow for generation of still higher economic value products from the gasifier associated with a Flexicoking™ process.

U.S. Patent 9,234,146 describes a process for gasification of heavy residual oil and coke from a. delayed coker unit. The gasification allow for production of synthesis gas from the heavy residual oil and coke. The gasifier used in the process corresponds to a membrane wail gasifier that uses an internal cooling screen that is protected by a layer of refractory material. The combination of the cooling screen and the layer of refractory material allows the slag formed during gasification to solidify and flow downward to the quench zone al the bottom of the reactor.

U.S. Pat. No. 7,919,065 describes systems and methods for producing ammonia and Fischer-Tropsch liquids based on gasification of a slurry of coal solids or petroleum coke. Slag is produced in the gasifier as a side product during gasification.

SUMMARY

In various aspects, a method is provided for producing synthesis gas or products derived from synthesis gas. The method can include exposing a feedstock comprising a T10 distillation point of 343° C. or more to a fluidized bed comprising solid particles in a reactor under thermal cracking conditions to form a 343° C.– liquid product. The solid particles can optionally be coke particles. The thermal cracking conditions can be effective for 10 wt % or more conversion of the feedstock relative to 343° C. The thermal cracking conditions can further be effective for depositing coke on the solid particles. One or more gas streams can be introduced into a gasifier. The one or more stream can include an oxygen stream comprising $O_2$, a diluent stream comprising $CO_2$, $H_2S$, other inorganic gases, or a combination thereof, and steam. The oxygen stream can include 55 vol % or more of $O_2$ prior to combining the oxygen stream with at least one of the diluent stream and the steam. At least a portion of the solid particles that include deposited coke can be passed from the reactor into the gasifier. In the gasifier, the solid particles comprising deposited coke can be exposed to gasification conditions to form a gas phase product and partially gasified coke particles. The gas phase product can include $H_2$, CO, and $CO_2$. Optionally, the gas phase product can include a combined volume of $H_2$ and CO that is greater than a volume of $N_2$ in the gas phase product. At least a first portion of the partially gasified coke particles can be removed from the gasifier. This can correspond to, for example, a particle purge to allow for removal of metals. At least a second portion of the partially gasified coke particles can be passed from the gasifier to the reactor. This can provide, for example, heat for performing the fluidized coking in the reactor.

In some aspects, the method can further include separating $CO_2$, $H_2S$, or a combination thereof from the gas phase product to form at least a synthesis gas stream. Optionally, at least a portion of the $CO_2$ and/or $H_2S$ separated from the gas phase product can be used to form a recycle stream. Such a recycle stream can be used to form at least a part of the diluent stream for the gasifier. Optionally, the synthesis gas stream can include 80 vol % or more of $H_2$ and CO.

In some aspects, the fluidized coking system can include a heater in addition to the gasifier. In such aspects, solid particles that include deposited coke from the reactor can optionally be passed through the heater on the way to the gasifier. Additionally or alternately, partially gasified coke particles from the gasifier can optionally be passed into the heater on the way to the reactor.

In some aspects, the first portion of partially gasified coke particles can include a first weight percentage of metals, such as a first weight percentage of nickel, vanadium, and/or iron, relative to a weight of the first portion of partially gasified coke particles. In such aspects, the first weight percentage of metals (or of nickel, vanadium, and/or iron) can be greater than a weight percentage of metals in the feedstock, relative to a weight of the feedstock. By purging partially gasified coke particles and by using a diluent, the amount of metal oxide deposition on the walls of the gasifier can be reduced or minimized. For example, exposing the solid particles including deposited coke to the gasification conditions can result in deposition of less than 0.1 wt % of metal oxides on a wall of the gasifier, relative to a metals content of the feedstock.

In some aspects, the gas phase product (or a portion of the gas phase product, such as a synthesis gas portion) can be used to form additional products. For example, at least a portion of the gas phase product can be exposed to a methanol synthesis catalyst under methanol synthesis conditions to form methanol. Additionally or alternately, nitrogen separated from air and/or nitrogen included in the oxygen stream to the gasifier can be used as a nitrogen source for ammonia production in the presence of an ammonia synthesis catalyst, optionally in conjunction with hydrogen derived from the gas phase product from the gasifier. Optionally, if both methanol and ammonia synthesis is being performed, the methanol and ammonia can be reacted in the presence of a urea synthesis catalyst to form urea.

In various aspects, a system is also provided for producing synthesis gas or products derived from synthesis gas. The system can include a fluidized bed coker comprising a coker feed inlet, a cold coke outlet, a hot coke inlet, and a liquid product outlet. The system can further include a gasifier comprising a gasifier coke inlet in fluid communication with the cold coke outlet, a gasifier coke outlet in fluid communication with the hot coke inlet, at least one gasifier input gas inlet, and a fuel gas outlet. It is noted that the fluid communication between the coker and the gasifier can be indirect, such as fluid communication via a heater. The system can further include a $CO_2$ separation stage comprising a separation stage inlet in fluid communication with the fuel gas outlet, a separation stage outlet in fluid communication with at least one gasifier input gas inlet, and a synthesis gas outlet. The system can further include an air separation unit comprising an oxygen stream outlet in fluid communication with the at least one gasifier input gas inlet and a nitrogen stream outlet. Optionally, the system can further include a methanol synthesis reactor, an ammonia synthesis reactor, and/or a urea synthesis reactor.

DETAILED DESCRIPTION

Figure 1:
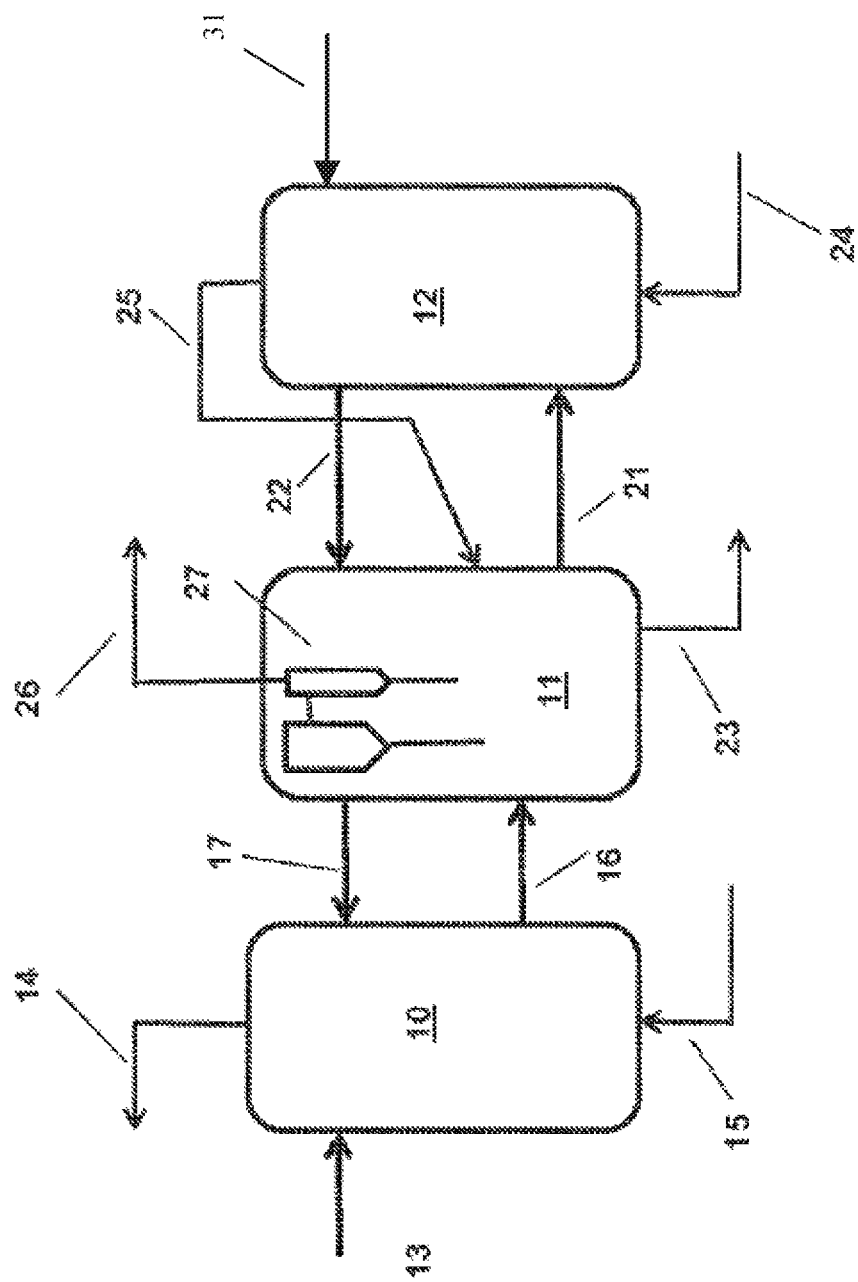
FIG. 1 shows an example of a fluidized bed coking system including a coker, a heater, and a gasifier.

All numerical values within the detailed description and the claims herein are modified by "about" or "approximately" the indicated value, and take into account experimental error and variations that would be expected by a person having ordinary skill in the art.

In this discussion, some feeds, fractions, or products may be described based on a fraction that boils below or above a specified distillation point. For example, a 343° C.− product corresponds to a product that contains components with a boiling point (at standard temperature and pressure) of 343° C. or less. Similarly, a 343° C.+ product corresponds to a product that contains components with a boiling point of 343° C. or more.

Overview

In various aspects, systems and methods are provided for producing high quality synthesis gas from a fluidized coking system that includes an integrated gasifier. Additionally or alternately, systems and methods are provided for integrating a fluidized coking process, a coke gasification process, and processes for production of compounds from the synthesis gas generated during the coke gasification. An example of a fluidized coking system with an integrated gasifier is a Flexicoking™ system available from Exxon Mobil Corporation. The integrated process can also allow for reduced or minimized production of inorganic nitrogen compounds by using oxygen from an air separation unit as the oxygen source for gasification. Although the amount of nitrogen introduced as a diluent into the gasification will be reduced, minimized, or eliminated, the integrated process can also allow for gasification of coke while reducing, minimizing, or eliminating production of slag or other glass-like substances in the gasifier. This can be achieved, for example, by recycling a portion of the $CO_2$ and/or $H_2S$ generated during gasification back to the gasifier. Additionally or alternately, other diluent compounds such as steam, CO, and/or other inorganic compounds (such as inorganic compounds that are non-reactive in the gasifier environment) can be used as well. Examples of compounds that can be produced from the synthesis gas include, but are not limited to, methanol, ammonia, and urea.

One of the difficulties with using petroleum coke, coal, and/or heavy oils as a feed for gasification is that such feeds can potentially contain a relatively high percentage of transition metals, such as iron, nickel, and vanadium. During conventional operation of a gasifier, these transition metals are converted into a "slag" that tends to be corrosive for the internal structures of the gasifier. As a result, gasifiers can typically have relatively short operating lengths between shutdown events, such as operating lengths of roughly 3 months to 18 months.

For an independently operated gasifier, frequent shutdown events may be acceptable. However, for a gasifier that is integrated to provide heat balance to another process, such as a fluidized bed coker, a short cycle length for the gasifier can force a short cycle length for the coker as well. In order to overcome this problem, a gasifier that is thermally integrated with a fluidized bed coking process, such as a Flexicoking™ process, can be operated under conditions that reduce, minimize, or eliminate formation of slag. Typically this can be achieved by using air as at least a major portion of the oxygen source for the gasifier that is integrated with the fluidized bed coking process. The additional nitrogen in air can provide a diluent for the gasifier environment that can reduce or minimize slag formation. Instead of forming a slag or other glassy type product containing metals, the metals in the coke can be retained in coke form and purged from the integrated system. This can allow removal or disposition of the metals to be performed in a secondary device or location. By avoiding formation of the corrosive slag, the cycle length of the integrated coker and gasifier can be substantially improved.

One difficulty with operating an integrated coker and gasifier to avoid slag formation is that the resulting fuel gas generated in the gasifier can have a relatively low BTU value. Because of the substantial amount of nitrogen introduced into the gasifier along with the oxygen, the nitrogen content of the fuel gas generated from an integrated fluidized bed/gasifier system can be up to ~55 vol %. This can present a variety of problems when attempting to find a high value use for the carbon in the fuel gas. For example, this low BTU gas includes a sufficient amount of diluent (such as nitrogen) that it is not directly suitable as a fuel in various types of burners in a refinery setting. Instead, use of the fuel gas as a fuel may require distribution of the fuel gas across multiple burners, so that the fuel gas can be blended with other fuels having a higher energy density. Another difficulty is that the low BTU gas is also a low pressure stream when it emerges from the gasifier. Attempting to compress the fuel gas to match pressures in another processing environment would require compressing the nitrogen in the fuel gas, meaning a substantial additional compression cost with little value in return. However, because the elevated levels of nitrogen make such a fuel gas generally undesirable and/or costly to use, such fuel gas is conventionally burned for heating value. Because this fuel gas is derived from coke that is processed in the gasifier, the net effect of burning this fuel gas is to convert a significant portion of the carbon (typically 20-40%) entering the coker into $CO_2$ that is released into the atmosphere. In various aspects, the systems and methods described herein can be beneficial for reducing or minimizing the amount of $CO_2$ that is exhausted into the atmosphere from a fluidized coking/gasifier system.

In various aspects, one or more of the above difficulties related to generation of a low BTU fuel gas from gasification in an integrated coker/gasifier can be overcome by modifying the oxygen source for the gasifier. Instead of using air as the oxygen source, an oxygen-containing stream can be generated by an air separation unit. An air separation unit can provide an oxygen stream with an oxygen content of 96 vol % or more. If desired, the air separation unit can be operated to generate a lower purity oxygen stream and/or additional nitrogen can be added to the oxygen stream so that the oxygen stream used for gasification can include 55 vol % or more of $O_2$, or 65 vol % or more, or 80 vol % or more of $O_2$. Thus, use of oxygen from an air separation unit as the oxygen source for a gasifier can reduce, minimize, and/or essentially eliminate the nitrogen content in the gasifier. By avoiding the introduction of substantial amounts of nitrogen into the gasifier, the nitrogen content of the fuel gas can also be reduced to a few percent or less. In various aspects, reducing the nitrogen introduced into the gasifier can allow the combined volume (or volume percentage) of $H_2$ and CO in the gas phase product from the gasifier to be greater than the volume (or volume percentage) of $N_2$ in the gas phase product.

While reducing the nitrogen content of the fuel gas can be beneficial, the nitrogen introduced into the gasifier also provided a benefit in the form of reducing or minimizing formation of slag or other glassy compounds in the gasifier. In order to maintain a reduced or minimized level of slag formation (such as no slag formation), an alternative diluent can instead be introduced into the gasifier. In various aspects, the alternative diluent can correspond to $CO_2$, $H_2S$, other inorganic compounds, or a combination thereof. Optionally, at least a portion of the alternative diluent can correspond to a recycle stream. Although gasification is typically performed under conditions with a limited amount of oxygen present in the reaction environment, at least some $CO_2$ is typically formed by the gasification reaction. Additionally, the water-gas shift equilibrium for syngas can potentially favor additional formation of $CO_2$, depending on the temperature and the relative concentrations of $H_2$, $H_2O$, CO, and $CO_2$. As a result, the fuel gas formed in the gasifier can include a substantial portion of $CO_2$. This $CO_2$ formed in the gasifier environment can be separated out by any convenient method, such as by use of a monoethanol amine wash or another type of amine wash. Conveniently, an amine wash can also be suitable for removal of any $H_2S$ that is formed during gasification (such as by reaction of $H_2$ with sulfur that is present in the coke). In some aspects, both $H_2S$ and $CO_2$ could be subsequently recovered during regeneration of the amine and fed to the gasifier as a diluent. In other aspects, multiple amine regeneration steps can be used to desorb $CO_2$ and $H_2S$ rich streams separately, thus allowing for control over the amount of recycled $CO_2$ or $H_2S$ rich streams that are delivered to the gasifier. In some aspects, $H_2S$ can be first removed using selective amine washing, such as a Flexsorb™ process, before using a more general amine was for $CO_2$ separation.

After separation of $CO_2$ and/or $H_2S$ from the fuel gas, a portion of the $CO_2$ and/or $H_2S$ can be recycled back to the gasifier as a diluent to reduce or minimize formation of slag. In some aspects, the net concentration of $O_2$ in the oxygen stream introduced into the gasifier, after addition of any diluent and/or steam, can be 30 vol % to 60 vol % relative to the weight of the combined oxygen stream plus diluent and/or steam. In some aspects, at least a portion of the $H_2S$ present in a $CO_2$ stream can be removed prior to recycling the $CO_2$ stream to the gasifier. This can assist with maintaining conditions in the gasifier that allow the metals and/or ash content of coke to be removed from the gasifier as part of a coke purge, as opposed to forming a corrosive slag. It is noted that $H_2S$ is reactive with oxygen and its direct injection into an oxygen rich stream should be avoided. Good distribution or mixing of fluidized coke and $H_2S$ can become important if a high level $H_2S$ recycling is used. To minimize syngas compression, preferably the amount of net $CO_2$ production that is above the desired level in the syngas can also be purged from the amine wash desorption step.

By reducing or minimizing the content of $N_2$ in the fuel gas while also reducing or minimizing slag formation by recycling $CO_2$ (and/or $H_2S$) to the gasifier, the fuel gas generated by an integrated coker/gasifier can have a substantially increased content of synthesis gas. After removal of sulfur contaminants, water, and/or $CO_2$, the resulting fuel gas can correspond to 70 vol % to 99 vol % of $H_2$ and CO, or 80 vol % to 95 vol %, which are the components of synthesis gas. This is a sufficient purity and/or a sufficiently high quality to potentially be valuable to use in synthesis of other compounds. For example, after optional exposure to a water gas-shift catalyst and/or addition of $H_2$, the synthesis gas can be used as a feed for methanol production.

In addition to methanol production, the type of configuration describe above can also be beneficial for ammonia production. The air separation unit used to generate the oxygen stream for gasification can also produce a high purity nitrogen stream. This high purity nitrogen stream can be combined with a hydrogen stream for ammonia production. In some aspects, the hydrogen can correspond to hydrogen from the synthesis gas generated by gasification. In some aspects, a separate $H_2$ source can be used to provide hydrogen for ammonia generation. In some aspects, a sufficient portion of $N_2$ can be left in the $O_2$ stream used for the gasifier so that the gasifier gas feeding an ammonia plant can also contain a major portion of the $N_2$ needed for ammonia production. For example, the amount of $N_2$ in the $O_2$ stream can be selected based on the amount of hydrogen available for ammonia production in the ammonia plant, or (if excess hydrogen is available) the amount of $N_2$ in the $O_2$ stream can be selected to provide a desired amount of ammonia production.

Fluidized Coking with Integrated Gasification

In this description, the term "Flexicoking" (trademark of ExxonMobil Research and Engineering Company) is used to designate a fluid coking process in which heavy petroleum feeds are subjected to thermal cracking in a fluidized bed of heated solid particles to produce hydrocarbons of lower molecular weight and boiling point along with coke as a by-product which is deposited on the solid particles in the fluidized bed. The resulting coke can then converted to a fuel gas by contact at elevated temperature with steam and an oxygen-containing gas in a gasification reactor (gasifier). This type of configuration can more generally be referred to as an integration of fluidized bed coking with gasification.

In various aspects, an integrated fluidized bed coker and gasifier, optionally also including a heater, can be used to process a feed by first coking the feed and then gasifying the resulting coke. This can generate a fuel gas product (withdrawn from the gasifier or the optional heater) that can then be further processed to increase the concentration of synthesis gas in the product. The product with increased synthesis gas concentration can then be used as an input for production of methanol, optionally after further processing to adjust the $H_2$ to CO ratio in the synthesis gas.

FIG. 1 shows an example of a Flexicoker unit (i.e., a system including a gasifier that is thermally integrated with a fluidized bed coker) with three reaction vessels: reactor, heater and gasifier. The unit comprises reactor section 10 with the coking zone and its associated stripping and scrubbing sections (not separately indicated), heater section 11 and gasifier section 12. The relationship of the coking zone, scrubbing zone and stripping zone in the reactor section is shown, for example, in U.S. Pat. No. 5,472,596, to which reference is made for a description of the Flexicoking unit and its reactor section. A heavy oil feed is introduced into the unit by line 13 and cracked hydrocarbon product withdrawn through line 14. Fluidizing and stripping steam is supplied by line 15. Cold coke is taken out from the stripping section at the base of reactor 10 by means of line 16 and passed to heater 11. The term "cold" as applied to the temperature of the withdrawn coke is, of course, decidedly relative since it is well above ambient at the operating temperature of the stripping section. Hot coke is circulated from heater 11 to reactor 10 through line 17. Coke from heater 11 is transferred to gasifier 12 through line 21 and hot, partly gasified particles of coke are circulated from the gasifier back to the heater through line 22. The excess coke is withdrawn from the heater 11 by way of line 23. In conventional configurations, gasifier 12 is provided with its supply of steam and air by line 24 and hot fuel gas is taken from the gasifier to the heater though line 25. In various aspects, instead of supplying air via a line 24 to the gasifier 12, a stream of oxygen with 55 vol % purity or more can be provided, such as an oxygen stream from an air separation unit. In such aspects, in addition to supplying a stream of oxygen, a stream of an additional diluent gas can be supplied by line 31. The additional diluent gas can correspond to, for example, $CO_2$ separated from the fuel gas generated during the gasification. The fuel gas is taken out from the unit through line 26 on the heater; coke fines are removed from the fuel gas in heater cyclone system 27 comprising serially connected primary and secondary cyclones with diplegs which return the separated fines to the fluid bed in the heater. The fuel gas from line 26 can then undergo further processing for separation of $CO_2$ (and/or $H_2S$) and conversion of synthesis gas to methanol.

It is noted that in some optional aspects, heater cyclone system 27 can be located in a separate vessel (not shown) rather than in heater 11. In such aspects, line 26 can withdraw the fuel gas from the separate vessel, and the line 23 for purging excess coke can correspond to a line transporting coke fines away from the separate vessel. These coke fines and/or other partially gasified coke particles that are vented from the heater (or the gasifier) can have an increased content of metals relative to the feedstock. For example, the weight percentage of metals in the coke particles vented from the system (relative to the weight of the vented particles) can be greater than the weight percent of metals in the feedstock (relative to the weight of the feedstock). In other words, the metals from the feedstock are concentrated in the vented coke particles. Since the gasifier conditions avoid the creation of slag, the vented coke particles correspond to the mechanism for removal of metals from the coker/gasifier environment. In some aspects, the metals can correspond to a combination of nickel, vanadium, and/or iron. Additionally or alternately, the gasifier conditions can cause substantially no deposition of metal oxides on the interior walls of the gasifier, such as deposition of less than 0.1 wt % of the metals present in the feedstock introduced into the coker/gasifier system, or less than 0.01 wt %.

In configurations such as FIG. 1, the system elements shown in the figure can be characterized based on fluid communication between the elements. For example, reactor section 10 is in direct fluid communication with heater 11. Reactor section 10 is also in indirect fluid communication with gasifier 12 via heater 11.

As an alternative, integration of a fluidized bed coker with a gasifier can also be accomplished without the use of an intermediate heater. In such alternative aspects, the cold coke from the reactor can be transferred directly to the gasifier. This transfer, in almost all cases, will be unequivocally direct with one end of the tubular transfer line connected to the coke outlet of the reactor and its other end connected to the coke inlet of the gasifier with no intervening reaction vessel, i.e. heater. The presence of devices other than the heater is not however to be excluded, e.g. inlets for lift gas etc. Similarly, while the hot, partly gasified coke particles from the gasifier are returned directly from the gasifier to the reactor this signifies only that there is to be no intervening heater as in the conventional three-vessel Flexicoker™ but that other devices may be present between the gasifier and the reactor, e.g. gas lift inlets and outlets.

Figure 2:
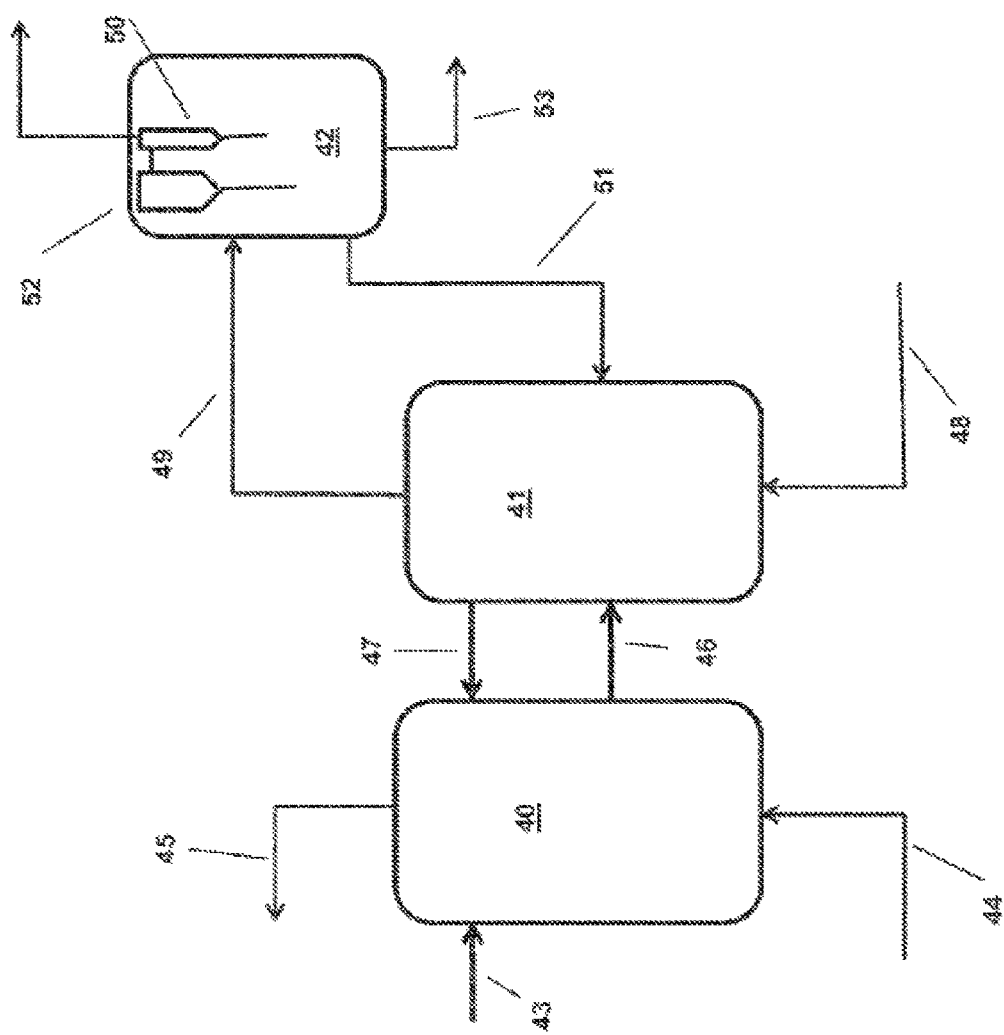
FIG. 2 shows an example of a fluidized bed coking system including a coker and a gasifier.

FIG. 2 shows an example of integration of a fluidized bed coker with a gasifier but without a separate heater vessel. In the configuration shown in FIG. 2, the cyclones for separating fuel gas from catalyst fines are located in a separate vessel. In other aspects, the cyclones can be included in gasifier vessel 41.

In the configuration shown in FIG. 2, the configuration includes a reactor 40, a main gasifier vessel 41 and a separator 42. The heavy oil feed is introduced into reactor 40 through line 43 and fluidizing/stripping gas through line 44; cracked hydrocarbon products are taken out through line 45. Cold, stripped coke is routed directly from reactor 40 to gasifier 41 by way of line 46 and hot coke returned to the reactor in line 47. Steam and oxygen are supplied through line 48. The flow of gas containing coke fines is routed to separator vessel 42 through line 49 which is connected to a gas outlet of the main gasifier vessel 41. The fines are separated from the gas flow in cyclone system 50 comprising serially connected primary and secondary cyclones with diplegs which return the separated fines to the separator vessel. The separated fines are then returned to the main gasifier vessel through return line 51 and the fuel gas product taken out by way of line 52. Coke is purged from the separator through line 53. The fuel gas from line 52 can then undergo further processing for separation of $CO_2$ (and/or $H_2S$) and conversion of synthesis gas to methanol.

The coker and gasifier can be operated according to the parameters necessary for the required coking processes. Thus, the heavy oil feed will typically be a heavy (high boiling) reduced petroleum crude; petroleum atmospheric distillation bottoms; petroleum vacuum distillation bottoms, or residuum; pitch; asphalt; bitumen; other heavy hydrocarbon residues; tar sand oil; shale oil; or even a coal slurry or coal liquefaction product such as coal liquefaction bottoms. Such feeds will typically have a Conradson Carbon Residue (ASTM D189-165) of at least 5 wt. %, generally from about 5 to 50 wt. %. Preferably, the feed is a petroleum vacuum residuum.

A typical petroleum chargestock suitable for processing in a fluidized bed coker can have a composition and properties within the ranges set forth below.

TABLE 1

| Example of Coker Feedstock | | |
| --- | --- | --- |
| Conradson Carbon | 5 to 40 | wt. % |
| API Gravity | −10 to 35° | |
| Boiling Point | 340° C.+ to 650° C.+ | |
| Sulfur | 1.5 to 8 | wt. % |
| Hydrogen | 9 to 11 | wt. % |
| Nitrogen | 0.2 to 2 | wt. % |
| Carbon | 80 to 86 | wt. % |
| Metals | 1 to 2000 | wppm |

More generally, the feed to the fluidized bed coker can have a T10 distillation point of 343° C. or more, or 371° C. or more.

The heavy oil feed, pre-heated to a temperature at which it is flowable and pumpable, is introduced into the coking reactor towards the top of the reactor vessel through injection nozzles which are constructed to produce a spray of the feed into the bed of fluidized coke particles in the vessel. Temperatures in the coking zone of the reactor are typically in the range of about 450° C. to about 850° C. and pressures are kept at a relatively low level, typically in the range of about 120 kPag to about 400 kPag (about 17 psig to about 58 psig), and most usually from about 200 kPag to about 350 kPag (about 29 psig to about 51 psig), in order to facilitate fast drying of the coke particles, preventing the formation of sticky, adherent high molecular weight hydrocarbon deposits on the particles which could lead to reactor fouling. The conditions can be selected so that a desired amount of conversion of the feedstock occurs in the fluidized bed reactor. The coking reaction and the amount of conversion can be selected to be similar to the values used in a conventional fluidized coking reaction. For example, the conditions can be selected to achieve at least 10 wt % conversion relative to 343° C. (or 371° C.), or at least 20 wt % conversion relative 343° C. (or 371° C.), or at least 40 wt % conversion relative to 343° C. (or 371° C.), such as up to 80 wt % conversion or possibly still higher. The light hydrocarbon products of the coking (thermal cracking) reactions vaporize, mix with the fluidizing steam and pass upwardly through the dense phase of the fluidized bed into a dilute phase zone above the dense fluidized bed of coke particles. This mixture of vaporized hydrocarbon products formed in the coking reactions flows upwardly through the dilute phase with the steam at superficial velocities of about 1 to 2 meters per second (about 3 to 6 feet per second), entraining some fine solid particles of coke which are separated from the cracking vapors in the reactor cyclones as described above. The cracked hydrocarbon vapors pass out of the cyclones into the scrubbing section of the reactor and then to product fractionation and recovery.

In this discussion, reference may be made to conversion of a feedstock relative to a conversion temperature. Conversion relative to a temperature can be defined based on the portion of the feedstock that boils at greater than the conversion temperature. The amount of conversion during a process (or optionally across multiple processes) can correspond to the weight percentage of the feedstock converted from boiling above the conversion temperature to boiling below the conversion temperature. As an illustrative hypothetical example, consider a feedstock that includes 40 wt % of components that boil at 650° F. (~343° C.) or greater. By definition, the remaining 60 wt % of the feedstock boils at less than 650° F. (~343° C.). For such a feedstock, the amount of conversion relative to a conversion temperature of ~343° C. would be based only on the 40 wt % that initially boils at ~343° C. or greater. If such a feedstock could be exposed to a process with 30% conversion relative to a ~343° C. conversion temperature, the resulting product would include 72 wt % of ~343° C.– components and 28 wt % of ~343° C.+ components.

As the cracking process proceeds in the reactor, the coke particles pass downwardly through the coking zone, through the stripping zone, where occluded hydrocarbons are stripped off by the ascending current of fluidizing gas (steam). They then exit the coking reactor and pass to the gasification reactor (gasifier) which contains a fluidized bed of solid particles and which operates at a temperature higher than that of the reactor coking zone. In the gasifier, the coke particles are converted by reaction at the elevated temperature with steam and an oxygen-containing gas into a fuel gas comprising carbon monoxide and hydrogen.

The gasification zone is typically maintained at a high temperature ranging from about 850° C. to about 1000° C. (about 1560° F. to 1830° F.) and a pressure ranging from about about 0 kPag to about 1000 kPag (about 0 psig to about 150 psig), preferably from about 200 kPag to about 400 kPag (about 30 psig to about 60 psig). Steam and an oxygen-containing gas having a low nitrogen content, such as oxygen from an air separation unit or another oxygen stream including 95 vol % or more of oxygen, or 98 vol % or more, are passed into the gasifier for reaction with the solid particles comprising coke deposited on them in the coking zone. A separate diluent stream, such as a recycled $CO_2$ or $H_2S$ stream derived from the fuel gas produced by the gasifier, can also be passed into the gasifier. The amount of diluent can be selected by any convenient method. For example, the amount of diluent can be selected so that the amount of diluent replaces the weight of $N_2$ that would be present in the oxygen-containing stream if air was used as the oxygen-containing stream. As another example, the amount of diluent can be selected to allow for replacement of the same BTU value for heat removal that would be available if $N_2$ was present based on use of air as the oxygen-containing stream. These types of strategy examples can allow essentially the same or a similar temperature profile to be maintained in the gasifier relative to conventional operation.

In the gasification zone the reaction between the coke and the steam and the oxygen-containing gas produces a hydrogen and carbon monoxide-containing fuel gas and a partially gasified residual coke product. Conditions in the gasifier are selected accordingly to generate these products. Steam, oxygen, and $CO_2$ rates will depend upon the rate at which cold coke enters from the reactor and to a lesser extent upon the composition of the coke which, in turn will vary according to the composition of the heavy oil feed and the severity of the cracking conditions in the reactor with these being selected according to the feed and the range of liquid products which is required. The fuel gas product from the gasifier may contain entrained coke solids and these are removed by cyclones or other separation techniques in the gasifier section of the unit; cyclones may be internal cyclones in the main gasifier vessel itself or external in a separate, smaller vessel as described below. The fuel gas product is taken out as overhead from the gasifier cyclones. The resulting partly gasified solids are removed from the gasifier and introduced directly into the coking zone of the coking reactor at a level in the dilute phase above the lower dense phase.

Methanol Production

After withdrawing the fuel gas from the heater or gasifier, the fuel gas can undergo further processing to produce a stream with an increased concentration of CO and $H_2$. Because a reduced or minimized amount of nitrogen was introduced into the gasifier as part of the oxygen stream, the amount of nitrogen in the fuel gas can also be minimal, such as 5 vol % or less. At this level, the nitrogen can be passed into a methanol synthesis process without requiring separation.

Other gases present in the fuel gas can be separated to improve the subsequent methanol synthesis process. For example, as noted above, the gasification conditions can result in formation of a substantial amount of $CO_2$, corresponding to about 5 vol % to 20 vol % of the fuel gas. This $CO_2$ can be removed from the fuel gas by any convenient method. Suitable methods for separation of $CO_2$ from the fuel gas can include, but are not limited to, amine washing and cryogenic separation. After separation of the $CO_2$ from the fuel gas, the $CO_2$ can be recovered (if necessary) and then used as in any convenient manner. In some aspects, at least a portion of the $CO_2$ can be used as a diluent for the gasification process. As discussed further below, $CO_2$ can potentially be converted to methanol under the methanol synthesis conditions, so complete removal of $CO_2$ is not necessary.

Another gas present in the fuel gas can be $H_2S$. For many types of heavy petroleum feeds, the feed can include a substantial amount of sulfur. This sulfur can be incorporated into the coke and then converted to $H_2S$ in the gasifier. Any convenient method for removal of $H_2S$ can be used. In aspects where an amine wash is used for $CO_2$ separation, the amine wash can also be effective for $H_2S$ removal.

During methanol synthesis, carbon monoxide and hydrogen can react over a catalyst to produce methanol. Commercial methanol synthesis catalysts can be highly selective, with selectivities of greater than 99.8% possible under optimized reaction conditions. Typical reaction conditions can include pressures of about 5 MPa to about 10 MPa and temperatures of about 250° C. to about 300° C. With regard to the syngas input for methanol synthesis, the preferred ratio of $H_2$ to CO (about 2:1 $H_2$:CO) does not match the typical ratio generated by a gasifier. For example, a typical Flexicoking™ $H_2$:CO ratio is about 1:1. In some aspects, production of methanol using syngas from a gasifier can be improved by addition of $H_2$ to the syngas. Additionally or alternatively, catalysts that facilitate methanol formation from syngas can sometimes additionally facilitate the water-gas shift reaction. As a result, the reaction scheme below shows that $CO_2$ can also be used to form methanol:

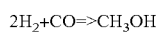

For methanol synthesis reactions, the composition of the synthesis gas input can be characterized by the Module value M:

$$M=[H_2—CO_2]/[CO+CO_2]$$

Module values close to 2 can generally be suitable for production of methanol, such as values of M that are at least about 1.7, or at least about 1.8, or at least about 1.9, and/or less than about 2.3, or less than about 2.2, or less than about 2.1. As can be noted from the Module Value equation above, in addition to the ratio of $H_2$ to CO, the ratio of CO to $CO_2$ in the syngas can impact the reaction rate of the methanol synthesis reaction.

The output stream from a gasifier can contain relatively high concentrations of $H_2$, CO, $CO_2$, and water. Through a combination of separations, (reverse) water gas shift reactions, and/or other convenient mechanisms, the composition of the fuel gas from the gasifier and/or a stream derived/withdrawn from the fuel gas can be adjusted. The adjustment of the composition can include removing excess water and/or $CO_2$, adjusting the ratio of $H_2$:CO, adjusting the Module value M, or a combination thereof. For example, a typical fuel gas from the gasifier may have an $H_2$:CO ratio of about 1:1. Removal of $CO_2$ from the fuel gas can facilitate a subsequent water gas shift reaction to increase this ratio to closer to 2:1 and/or to increase the Module value M of the stream to closer to 2.

In a typical methanol plant, a large percentage of the reactor exhaust can be recycled after recovery of methanol liquid, due to low conversion per pass. In some configurations, the output from the methanol synthesis reaction can be separated into a liquid alcohol product, a recycle syngas stream, and a vented purge. The vented purge can contain syngas components, fuel components (e.g. methane), and inerts. In some aspects, at least a portion of the vented purge can be used to raise steam for heating the syngas production. Additionally or alternatively, at least a portion of the purged gas can be upgraded to syngas in the gasifier of the coker. Further additionally or alternatively, the water produced in the methanol plant can be used as wash water in the coker light product recovery section.

Ammonia Production

Ammonia can typically be made from $H_2$ and $N_2$ via the Haber-Bosch process at elevated temperature and pressure. Conventionally, the inputs can be a) purified $H_s$, which can be made from a multi-step process that can typically require steam methane reforming, water gas shift, water removal, and trace carbon oxide conversion to methane via methanation; and b) purified $N_2$, which can typically be derived from air via pressure swing adsorption and/or an air separation unit.

Additionally or alternately, the purified $H_2$ for ammonia production can be provided from the syngas generated by the gasifier (as part of the fuel gas). As described above, the syngas generated by the gasifier can be further processed to remove impurities such as sulfur. For ammonia synthesis, the hydrogen stream can preferably be substantially free of impurities such as $H_2S$. If a portion of the syngas generated by the gasifier is used as a source of hydrogen for ammonia synthesis, the syngas can first be reacted in a water-gas shift reactor to maximize the amount of $H_2$ relative to CO. Water-gas shift is a well-known reaction, and typically can be done at "high" temperatures (from about 300° C. to about 500° C.) and "low" temperatures (from about 100° C. to about 300° C.) with the higher temperature catalyst giving faster reaction rates, but with higher exit CO content, followed by the low temperature reactor to further shift the syngas to higher $H_2$ concentrations. Following this, the gas can undergo separation via one or more processes to purify the $H_2$. This can involve, for example, condensation of the water, removal of $CO_2$, purification of the $H_2$ and then a final methanation step at elevated pressure (typically about 15 barg to about 30 barg, or about 1.5 MPag to about 3 MPag) to ensure that as many carbon oxides as possible can be eliminated. Lastly, the $H_2$ stream can be compressed to ammonia synthesis conditions of about 60 barg (about 6 MPag) to about 180 barg (about 18 MPag). Typical ammonia processes can be performed at about 350° C. to about 500° C., such as at about 450° C. or less, and can result in low conversion per pass (typically less than about 20%) and a large recycle stream.

In some aspects, the gasification $CO_2$ recirculation system described herein can also incorporate a purge $CO_2$ stream to reduce or minimize the need for $CO_2$ separation or destruction at high pressure before the ammonia plant. In some aspects, the purge stream from the ammonia plant can be recycled to gasifier for additional recovery of synthesis gas.

Urea is another large chemical product that can be made by the reaction of ammonia with $CO_2$. The basic process, developed in 1922, is also called the Bosch-Meiser urea process after its discoverers. The various urea processes can be characterized by the conditions under which urea formation takes place and the way in which unconverted reactants are further processed. The process can consist of two main equilibrium reactions, with incomplete conversion of the reactants. The net heat balance for the reactions can be exothermic. The first equilibrium reaction can be an exothermic reaction of liquid ammonia with dry ice (solid $CO_2$) to form ammonium carbamate ($H_2N$—$COONH_4$):

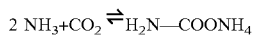

The second equilibrium reaction can be an endothermic decomposition of ammonium carbamate into urea and water:

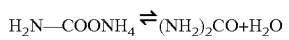

The urea process can use liquefied ammonia and $CO_2$ at high pressure as process inputs. In prior art processes, carbon dioxide is typically provided from an external resource where it must be compressed to high pressure. In contrast, the current process, as shown in FIG. 6, can produce a high pressure carbon dioxide stream suitable for reaction with the liquid ammonia product from the ammonia synthesis reaction. It is noted that the gasification $O_2$ input can be varied to adjust the amount of $CO_2$ produced. In addition, CO produced in the gasification step and steam can be reacted to produce more $H_2$ and $CO_2$ for $NH_3$ and increased urea production.

In various aspects, the urea process can be integrated into a combined system with an ammonia synthesis process and a Flexicoker™ type process (i.e., fluidized bed coker including an integrated gasifier). This integrated approach can reduce and/or eliminate many processes from the conventional approach, which can require an ammonia plant (steam reformer, water gas shift, pressure swing adsorption to produce $H_2$+air separation plant) plus a separate supply of $CO_2$ typically made remotely and then transported to the plant. The current system can eliminate many of these processes, as well as providing $CO_2$ for use in forming the urea. Specifically, rather than transport $CO_2$ as dry ice for use at a remote urea plant, carbon dioxide can be provided from separation of the syngas stream from the gasifier.

CONFIGURATION EXAMPLE

Modification of Operation of Gasifier for Production of Synthesis Gas

Figure 3:
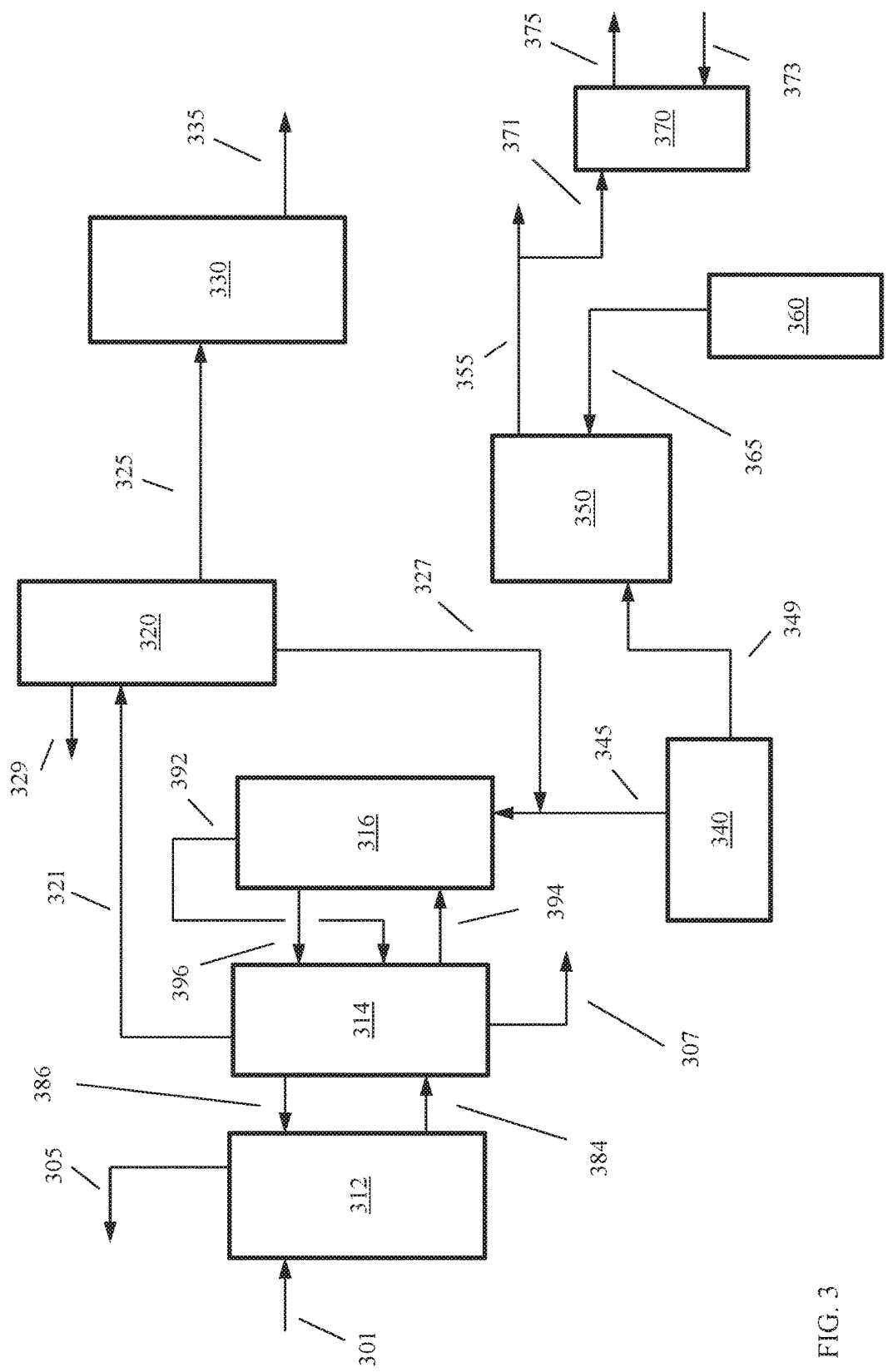
FIG. 3 schematically shows an example of a configuration for integrating fluidized coking with production of methanol, ammonia, and/or other products derived at least in part from a synthesis gas.

FIG. 3 shows an example of a configuration that provides an integrated fluidized bed coker and gasifier, along with optional methanol synthesis, ammonia synthesis, and urea synthesis processes. It is noted that any convenient combination of the methanol synthesis, ammonia synthesis, and urea synthesis processes can be present independently from each other. To the degree that an output of one optional process (such as ammonia) is described as being an input for a second optional process (such as urea synthesis), it is understood that in some aspects, the input for the second optional process can be derived from another conventional source.

In FIG. 3, a feed 301 suitable for coking is introduced into fluidized bed coker 312. The feed 301 can correspond to a heavy oil feed, or any other convenient feed typically used as an input for a coker. In the configuration shown in FIG. 3, the fluidized bed coker 312 is integrated with a heater 314 and a gasifier 316. This combination of elements is similar to the configuration shown in FIG. 1.

In FIG. 3, fluidized bed coker 312 generates a primary product 305 that includes fuel boiling range liquids generated during the coking process. Heat for coker 312 is provided by hot coke recycle line 386, while cold coke from coker 312 is passed into heater 314 via line 384. Coke from heater 314 is transferred to gasifier 316 through line 394 and hot, partly gasified particles of coke are circulated from the gasifier back to the heater through line 396. Fuel gas generated in gasifier 316 is returned to heater 314 via line 392. It is noted that gasifier 316 generally does not generate a slag that is separately removed from the gasifier. Instead, excess coke is withdrawn from the heater 314 by way of line 307. It is noted that the steam lines for fluidization of the coke in the fluidized bed and the gasifier are not shown in FIG. 3.

Fuel gas provided from gasifier 316 to heater 314 via line 392 can provide the fluidization needed in heater 314. The fuel gas can be withdrawn from heater 314 via line 321, optionally after passing through cyclone separators (not shown) for removal of coke fines from the fuel gas. The fuel gas in line 321 can be passed into a separation stage 320 for separation of $CO_2$ from the fuel gas. A portion of the $CO_2$ can be vented and/or withdrawn via line 329 for use in any convenient manner. Another portion of the $CO_2$ 327 can be used a recycle stream and returned to gasifier 316. In the configuration shown in FIG. 3, this is accomplished by combining the portion of the $CO_2$ 327 with oxygen 345 from air separation unit 340. The combined oxygen 345 and $CO_2$ 327 are then passed into gasifier 316. Optionally, separation stage 320 can also be used for removal of $H_2S$ from the fuel gas stream 321. Optionally, one or more additional separation stages may be present if removal of any other impurities from fuel gas stream 321 is desired. After separation of $CO_2$ (and/or other impurities), the remaining portion of the fuel gas stream can correspond to a synthesis gas stream 325. The synthesis gas stream 325 can be passed into a methanol synthesis plant 330 for production of methanol 335.

In addition to providing a high purity oxygen stream 345 to gasifier 316, the air separation unit 340 can also generate a nitrogen stream 349 that has a nitrogen content of 95 vol % or more. This can be passed into an ammonia synthesis process 350. The ammonia synthesis process 350 can also receive a hydrogen stream 365 corresponding to 98 vol % or more of hydrogen. In FIG. 3, hydrogen stream 365 is provided from a hydrogen source 360. Optionally, hydrogen stream 365 can be derived at least in part from synthesis gas stream 325. The hydrogen stream 365 and nitrogen stream 349 can be reacted in ammonia synthesis process 350 to form ammonia output 355. Optionally, a portion 371 of ammonia output 355 can be passed into a urea synthesis process 370 for production of a urea stream 375. The urea synthesis process 370 can also require a stream of $CO_2$ 373. Optionally, at least a portion of $CO_2$ stream 373 can correspond to $CO_2$ derived from $CO_2$ vent and/or withdrawal stream 329.

Additional Embodiments

Embodiment 1. A method for producing synthesis gas or products derived from synthesis gas, comprising: exposing a feedstock comprising a T10 distillation point of 343° C. or more to a fluidized bed comprising solid particles in a reactor under thermal cracking conditions to form a 343° C.– liquid product, the solid particles optionally comprising coke, the thermal cracking conditions comprising about 10 wt % or more conversion of the feedstock relative to 343° C. (or 20 wt % or more, or 40 wt % or more), the thermal cracking conditions being effective for depositing coke on the solid particles; introducing an oxygen stream comprising $O_2$, a diluent stream comprising $CO_2$, $H_2S$, other inorganic gases, or a combination thereof, and steam into a gasifier, the oxygen stream comprising 55 vol % or more of $O_2$ prior to combining the oxygen stream with at least one of the diluent stream and the steam; passing at least a portion of the solid particles comprising deposited coke from the reactor to the gasifier; exposing the at least a portion of the solid particles comprising deposited coke to gasification conditions in the gasifier to form a gas phase product comprising $H_2$, CO, and $CO_2$ and partially gasified coke particles, the gas phase product comprising a combined volume of $H_2$ and CO that is greater than a volume of $N_2$ in the gas phase product; removing at least a first portion of the partially gasified coke particles from the gasifier; and passing at least a second portion of the partially gasified coke particles from the gasifier to the reactor, wherein the oxygen stream is optionally combined with the at least one of the diluent stream and the steam in the gasifier and/or prior to entering the gasifier.

Embodiment 2. The method of Embodiment 1, further comprising separating $CO_2$, $H_2S$, or a combination thereof from the gas phase product to form at least a synthesis gas stream.

Embodiment 3. The method of Embodiment 2, wherein the diluent stream comprises a recycled portion of the $CO_2$, $H_2S$, or a combination thereof separated from the gas phase product; or wherein the synthesis gas stream comprises 80 vol % or more of $H_2$ and CO; or a combination thereof Embodiment 4. The method of any of the above embodiments, a) wherein passing at least a portion of the solid particles comprising deposited coke from the reactor to the gasifier comprises passing the at least a portion of the solid particles comprising deposited coke to a heater, and passing the at least a portion of the solid particles comprising deposited coke from the heater to the gasifier; b) wherein passing at least a second portion of the partially gasified coke particles from the gasifier to the reactor comprises passing the at least a second portion of partially gasified coke particles to a heater, and passing the at least a second portion of the partially gasified coke particles from the heater to the reactor; or c) a combination of a) and b).

Embodiment 5. The method of any of the above embodiments, wherein the first portion of partially gasified coke particles comprises a first weight percentage of metals, relative to a weight of the first portion of partially gasified coke particles, that is greater than a weight percentage of metals in the feedstock, relative to a weight of the feedstock; or wherein the first portion of partially gasified coke particles comprises a first combined weight percentage of nickel, vanadium, and iron, relative to a weight of the first portion of partially gasified coke particles, that is greater than a combined weight percentage of nickel, vanadium, and iron in the feedstock, relative to a weight of the feedstock; or a combination thereof Embodiment 6. The method of any of the above embodiments, wherein the exposing the at least a portion of the solid particles comprising coke to gasification conditions results in deposition of less than 0.1 wt % of metal oxides on a wall of the gasifier, relative to a metals content of the feedstock.

Embodiment 7. The method of any of the above embodiments, further comprising exposing at least a portion of the gas phase product to a methanol synthesis catalyst under methanol synthesis conditions to form methanol.

Embodiment 8. The method of any of the above embodiments, further comprising: separating the oxygen stream and a nitrogen stream from air, the nitrogen stream comprising 95 vol % or more of $N_2$; and exposing at least a portion of the nitrogen stream to a catalyst in the presence of $H_2$ under ammonia synthesis conditions to form ammonia.

Embodiment 9. The method of Embodiment 8, wherein exposing at least a portion of the nitrogen stream to an ammonia synthesis catalyst in the presence of $H_2$ under ammonia synthesis conditions comprises exposing at least a portion of the nitrogen stream and at least a portion of the synthesis gas stream to the ammonia synthesis catalyst under ammonia synthesis conditions.

Embodiment 10. The method of Embodiment 8 or 9, further comprising exposing at least a portion of the ammonia to a urea synthesis catalyst in the presence of $CO_2$ under urea synthesis conditions to form urea, and optionally further comprising separating $CO_2$, $H_2S$, or a combination thereof from the gas phase product to form a $CO_2$ product stream, wherein exposing at least a portion of the ammonia to a urea synthesis catalyst in the presence of $CO_2$ under urea synthesis conditions comprises exposing at least a portion of the ammonia and at least a portion of the $CO_2$ product stream to the urea synthesis catalyst under urea synthesis conditions.

Embodiment 11. A system producing synthesis gas or products derived from synthesis gas, comprising: a fluidized bed coker comprising a coker feed inlet, a cold coke outlet, a hot coke inlet, and a liquid product outlet; a gasifier comprising a gasifier coke inlet in fluid communication with the cold coke outlet, a gasifier coke outlet in fluid communication with the hot coke inlet, at least one gasifier input gas inlet, and a fuel gas outlet; a $CO_2$ separation stage comprising a separation stage inlet in fluid communication with the fuel gas outlet, a separation stage outlet in fluid communication with at least one gasifier input gas inlet, and a synthesis gas outlet; and an air separation unit comprising an oxygen stream outlet in fluid communication with the at least one gasifier input gas inlet and a nitrogen stream outlet.

Embodiment 12. The system of Embodiment 11, further comprising a heater, the gasifier coke inlet being in indirect fluid communication with the cold coke outlet via the heater, the gasifier coke outlet being in indirect fluid communication with the hot coke inlet via the heater.

Embodiment 13. The system of Embodiment 11 or 12, further comprising a methanol synthesis reactor comprising a synthesis gas inlet in fluid communication with the synthesis gas outlet.

Embodiment 14. The system of any of Embodiments 11 to 13, further comprising an ammonia synthesis reactor comprising a nitrogen inlet in fluid communication with the nitrogen stream outlet, the ammonia synthesis reactor optionally further comprising a hydrogen inlet in fluid communication with the synthesis gas outlet.

Embodiment 15. The system of Embodiment 14, wherein the ammonia synthesis reactor further comprises an ammonia outlet, the system further comprising a urea synthesis reactor comprising an ammonia inlet in fluid communication with the ammonia outlet and a $CO_2$ inlet in fluid communication with the separation stage outlet.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for producing synthesis gas or products derived from synthesis gas, comprising:

exposing a feedstock comprising a T10 distillation point of 343° C. or more to a fluidized bed comprising solid particles in a reactor under thermal cracking conditions to form a 343° C.-liquid product, the thermal cracking conditions comprising 10 wt % or more conversion of the feedstock relative to 343° C., the thermal cracking conditions being effective for depositing coke on the solid particles;

introducing an oxygen stream comprising $O_2$, a diluent stream comprising $CO_2$, $H_2S$, other inorganic gases, or a combination thereof, and steam into a gasifier, the oxygen stream comprising 55 vol % or more of $O_2$ prior to combining the oxygen stream with at least one of the diluent stream and the steam;

passing at least a portion of the solid particles comprising deposited coke from the reactor to the gasifier;

exposing the at least a portion of the solid particles comprising deposited coke to gasification conditions in the gasifier to form a gas phase product comprising $H_2$, CO, and $CO_2$ and partially gasified coke particles, the gas phase product comprising a combined volume of $H_2$ and CO that is greater than a volume of $N_2$ in the gas phase product;

removing at least a first portion of the partially gasified coke particles from the gasifier; and passing at least a second portion of the partially gasified coke particles from the gasifier to the reactor.

2. The method of claim 1, further comprising separating $CO_2$, $H_2S$, or a combination thereof from the gas phase product to form at least a synthesis gas stream.

3. The method of claim 2, wherein the diluent stream comprises a recycled portion of the $CO_2$, $H_2S$, or a combination thereof separated from the gas phase product; or wherein the synthesis gas stream comprises 80 vol % or more of $H_2$ and CO; or a combination thereof.

4. The method of claim 1, wherein passing at least a portion of the solid particles comprising deposited coke from the reactor to the gasifier comprises passing the at least a portion of the solid particles comprising deposited coke to a heater, and passing the at least a portion of the solid particles comprising deposited coke from the heater to the gasifier.

5. The method of claim 1, wherein passing at least a second portion of the partially gasified coke particles from the gasifier to the reactor comprises passing the at least a second portion of partially gasified coke particles to a heater, and passing the at least a second portion of the partially gasified coke particles from the heater to the reactor.

6. The method of claim 1, wherein the oxygen stream is combined with at least a portion of the diluent stream prior to introducing the oxygen stream into the gasifier, or wherein the oxygen stream is combined with at least a portion of the diluent stream upstream from the gasifier.

7. The method of claim 1, wherein the first portion of partially gasified coke particles comprises a first weight percentage of metals, relative to a weight of the first portion of partially gasified coke particles, that is greater than a weight percentage of metals in the feedstock, relative to a weight of the feedstock; or wherein the first portion of partially gasified coke particles comprises a first combined weight percentage of nickel, vanadium, and iron, relative to a weight of the first portion of partially gasified coke particles, that is greater than a combined weight percentage of nickel, vanadium, and iron in the feedstock, relative to a weight of the feedstock; or a combination thereof.

8. The method of claim 1, wherein the exposing the at least a portion of the solid particles comprising coke to gasification conditions results in deposition of less than 0.1 wt % of metal oxides on a wall of the gasifier, relative to a metals content of the feedstock.

9. The method of claim 1, wherein the solid particles comprise coke.

10. The method of claim 1, further comprising exposing at least a portion of the gas phase product to a methanol synthesis catalyst under methanol synthesis conditions to form methanol.

11. The method of claim 1, further comprising:
separating the oxygen stream and a nitrogen stream from air, the nitrogen stream comprising 95 vol % or more of $N_2$; and
exposing at least a portion of the nitrogen stream to a catalyst in the presence of $H_2$ under ammonia synthesis conditions to form ammonia.

12. The method of claim 11, wherein exposing at least a portion of the nitrogen stream to an ammonia synthesis catalyst in the presence of $H_2$ under ammonia synthesis conditions comprises exposing at least a portion of the nitrogen stream and at least a portion of the synthesis gas stream to the ammonia synthesis catalyst under ammonia synthesis conditions.

13. The method of claim 11, further comprising exposing at least a portion of the ammonia to a urea synthesis catalyst in the presence of $CO_2$ under urea synthesis conditions to form urea.

14. The method of claim 13, further comprising separating $CO_2$, $H_2S$, or a combination thereof from the gas phase product to form a $CO_2$ product stream, wherein exposing at least a portion of the ammonia to a urea synthesis catalyst in the presence of $CO_2$ under urea synthesis conditions comprises exposing at least a portion of the ammonia and at least a portion of the $CO_2$ product stream to the urea synthesis catalyst under urea synthesis conditions.

* * * * *